United States Patent [19]

Igarashi et al.

[11] Patent Number: 5,948,749
[45] Date of Patent: Sep. 7, 1999

[54] PHARMACEUTICAL PREPARATIONS FOR INTRANASAL ADMINISTRATION

[75] Inventors: Rie Igarashi; Mitsuko Takenaga, both of Kawasaki; Hiroshi Muramatsu, Hino; Tetsuo Ebata, Kunitachi; Yasuo Kosaka, Matsudo, all of Japan

[73] Assignee: Fuji Yakuhin Company, Limited, Japan

[21] Appl. No.: 08/922,775

[22] Filed: Sep. 3, 1997

[30] Foreign Application Priority Data

Oct. 7, 1996 [JP] Japan ................................. 8-282866

[51] Int. Cl.$^6$ .................................................. A61K 38/00
[52] U.S. Cl. ............................ 514/2; 514/12; 424/489; 424/499; 424/501
[58] Field of Search .................. 514/2, 42; 424/489, 424/499, 501

[56] References Cited

U.S. PATENT DOCUMENTS

| | | | |
|---|---|---|---|
| 4,250,163 | 2/1981 | Nagai | 424/14 |
| 5,112,804 | 5/1992 | Kowarski | 514/3 |
| 5,158,761 | 10/1992 | Kamishita | 424/45 |
| 5,204,108 | 4/1993 | Illum | 424/434 |
| 5,342,922 | 8/1994 | Marshall | 530/329 |
| 5,397,771 | 3/1995 | Bechgaard | 514/2 |
| 5,554,388 | 9/1996 | Illum | 424/501 |
| 5,604,257 | 2/1997 | Tabe | 514/460 |
| 5,675,031 | 10/1997 | Furuya | 560/53 |

*Primary Examiner*—Cecilia J. Tsang
*Assistant Examiner*—David Lukton
*Attorney, Agent, or Firm*—Price, Heneveld, Cooper, Dewitt & Litton

[57] ABSTRACT

A pharmaceutical preparation for intranasal administration having a better absorption rate and less irritant effects is provided. The pharmaceutical preparation comprises a mixture of a powder of an adsorbent resin and a biologically active peptide having a drug effect under the condition that they are dry prior to or after the mixing.

23 Claims, 6 Drawing Sheets

STYRENE - DIVINYLBENZENE COPOLYMER RESIN / INSULIN MIXED PRODUCT

POLYMETHACRYLATE RESIN/
INSULIN MIXED PRODUCT

FIG. 3

STYRENE-DIVINYLBENZENE COPOLYMER RESIN / INSULIN MIXED PRODUCT

| (min) | 0 | 10 | 20 | 30 | 60 | 90 |
|---|---|---|---|---|---|---|
| BLOOD GLUCOSE LEVEL(mg/dl) | 0 | -2.5 | 3 | -15.5 | -11.5 | -10 |
| IRI (μU/ml) | 0 | 10.6 | 9.4 | 5.1 | 3.7 | 2.3 |

FIG. 4

POLYMETHACRYLATE RESIN / INSULIN MIXED PRODUCT

| (min) | 0 | 10 | 20 | 30 | 60 | 90 |
|---|---|---|---|---|---|---|
| BLOOD GLUCOSE LEVEL(mg/dl) | 0 | -1.5 | -2.5 | -5 | -2 | -4.5 |
| IRI (μU/ml) | 0 | 2 | 1.1 | 1.5 | 1.2 | -0.7 |

FIG. 5

EFFECT ON FASTING BLOOD SUGAR
LEVEL OF A NORMAL SUBJECT

FIG. 6

POSTPRANDIAL HYPERGLYCEMIC ACTION
INHIBITORY EFFECT ON A NORMAL SUBJECT

FIG. 7

EFFECT ON FASTING BLOOD SUGAR LEVEL

|  | BEFORE ADMINISTRATION | 30 MIN. AFTER ADMINISTRATION | DIFFERENCE |
|---|---|---|---|
| PERNASAL ADMINISTRATION 1 (10 mg) | 105 | 90 | -15 |
| PERNASAL ADMINISTRATION 2 (15 mg) | 94 | 76 | -18 |
| PERNASAL ADMINISTRATION 3 (20 mg) | 86 | 73 | -13 |
| CONTROL | 92 | 94 | 2 |

EFFECT ON POSTPRANDIAL BLOOD SUGAR LEVEL

|  | BEFORE | 60 MIN. AFTER MEAL | DIFFERENCE |
|---|---|---|---|
| PERNASAL ADMINISTRATION | 98 | 167 | 69 |
| PERNASAL ADMINISTRATION | 90 | 177 | 87 |
| PERNASAL ADMINISTRATION | 100 | 144 | 44 |
| (AVERAGE) | 96 | 163 | 67 |
| CONTROL | 89 | 178 | 89 |
| CONTROL | 90 | 189 | 99 |
| (AVERAGE) | 89.5 | 183.5 | 94 |

OPHTHALMIC MUCOUS MEMBRANE IRRITATION CLASSIFICATION ACCORDING TO THE METHOD OF KAY AND CALANDRA (1962)

| TOTAL | EVALUATION |
|---|---|
| 0.0 - 0.5 | NON-IRRITATING |
| 0.5 - 2.5 | PRACTICALLY NON-IRRITATING |
| 2.5 - 15 | MINIMALLY IRRITATING |
| 15 - 25 | MIDLY IRRITATING |
| 25 - 50 | MODERATELY IRRITATING |
| 50 - 80 | SEVERELY IRRITATING |
| 80 - 100 | EXTREMELY IRRITATING |
| 100 - 100 | MAXIMALLY IRRITATING |

AT THE BOUNDARY, A HIGHER EVALUATION IS GIVEN.

PHARMACEUTICAL PREPARATIONS FOR INTRANASAL ADMINISTRATION

BACKGROUND OF THE INVENTION

1. Field of the Invention

The present invention relates to a pharmaceutical preparation for intranasal administration comprising a mixture of a powder of an adsorbent resin and a biologically active peptide having pharmacological effects, which are prepared under the dry condition prior to or after mixing.

2. Description of the Related Art

Recently, a noninjection type medication method has been desired to be developed for a biologically active peptide having pharmacological effects which allows self-administration by patients and assures the prolonged action of the drug.

It is recognized that the peptide type drugs hardly provide enough bioavailability to assure the drug effect when it is administered by other administration routes than injection, such as oral, percutaneous, intrarectal or sublingual administration. Therefore, there have been attempts to select the nasal mucosa as the administration site to carry out intranasal administration of peptide type drugs to attain enough bioavailability to show their pharmacological effects.

One of such attempts is shown in Japanese Patent Application No. 7-197919. The technology used in this application is intranasal administration in which a vaccine or a biologically active peptide having pharmacological effects is mixed with an ion-exchange resin or an adsorption resin powder (each used alone or in admixture of two or more kinds) and the resulting suspension or a powder is administered, and the ion-exchange resin and the adsorbent resin are claimed; however, the mechanism of the absorption has been explained that the insulin is liberated on the mucosal surface by the repelling force between the ions and absorbed across the mucosa.

This mechanism can apply to the ion-exchange resin, but cannot apply to the adsorbent resin which does not have an ionic active group. And the mechanism for the adsorbent resin has not been clarified in the above-mentioned Japanese Patent Application No. 7-197919.

SUMMARY OF THE INVENTION

As a result of the study, the present inventors found electrostatic attractive force as the absorbing mechanism of the adsorbent resin. That means, the adsorbent resin and insulin powder (a biologically active peptide having pharmacological effects and an other drug with electrostatic charge than the peptide) are attracted by the attractive force due to the static electricity and as a result, the adsorbent resin which is the carrier adheres the insulin (a biologically active peptide having pharmacological effects and an other drug with electrostatic charge than the peptide). Dryness is the required condition for this adhesion. When contacted with the mucosal surface, the electrostatic attractive force is lost by the moisture and insulin is liberated. Here, the inventors found that a nonpolar adsorbent resin (illustratively, styrene-divinylbenzene copolymer) having no polarity liberates insulin more easily, in other words causes better absorption, than the polar substance, illustratively, a methacrylate polymer.

In addition to good absorbability, no or less irritation to the nasal mucosa is another important requirement for the intranasal administered drug. The ion-exchange resin having an ionic active group caused moderate irritation to the mucosa, but the adsorbent resin had less irritant action and particularly the non-polar adsorbent resin having no polarity was found to have almost no irritant effects to the mucosa.

As described above, an object of the present invention is to provide a pharmaceutical preparation for intranasal administration having better absorbability and less irritant effects by discovering the electrostatic attractive force as the absorption mechanism of the adsorbent resin, which has not been cleared in the Japanese Patent Application No. 7-197919.

There is no particular limitation in a process for allowing the powder carrier of the adsorbent resin to adsorb the biologically active peptide having pharmacological effects, as far as the both substances can be physically mixed homogeneously and stably. Provided that since the attractive force of the adsorption is the static electricity, they must be as dry as possible in the mixed conditions.

Examples of the mixing process include 1) simple mixing of a biologically active peptide powder having pharmacological effects which has been dried under drying conditions with a dried adsorbent resin powder by simple stirring or using a mortar or a ball mill. 2) An adsorbent resin powder is added to an aqueous solution or suspension of a biologically active peptide having pharmacological effects and a mixed suspension is obtained. Thereafter, it is dried by evaporation to provide a powder. 3) During the mixing of the powders of process 1), an organic solvent such as ethanol is added to improve homogeneity of the mixture.

For administering the powder preparation of the present invention into the nasal cavity, it is necessary that the preparation has no irritant effects on the administration site, does not provide any foreign body sensation, and scatters appropriate by so that it can be distributed and adhered on the nasal mucosa as uniformly as possible when it is nebulized. As the thickness of the mucous layer on the nasal mucosa is 5–11 $\mu$m, the particle should not be too large. Accordingly, an average particle size of the powder of the adsorbent resin used according to the present invention is 100 $\mu$m–10 $\mu$m, more preferably 10–70 $\mu$m, still more preferably 20–50 $\mu$m. Examples of the adsorbent resin include a nonpolar adsorbent resin having styrene-divinylbenzene as its basic skeleton, such as styrene-divinylbenzene copolymer, a slightly polar resin having a methacrylic ester as its basic skeleton, and a polar adsorbent resin having vinyl pyridine and sulphoxide amide amino acid and the like as its basic skeleton, but a preferable adsorbent resin used according to the present invention is a nonpolar adsorbent resin such as a styrene-divinylbenzene copolymer.

The biologically active peptide having pharmacological effects which is adhered on the adsorbent resin carrier in the pharmaceutical preparation of the present invention needs to remain stably adhered on the carrier during the storage in the form of the pharmaceutical preparations, but once nebulized onto the nasal mucosa, it should be easily liberated from the carrier and dissolved into the mucosa and absorbed therefrom. Accordingly, their particle size is desirably smaller than that of the carrier and it is 10 $\mu$m–0.001 $\mu$m, preferably it is 1 $\mu$m–0.001 $\mu$m.

The dose of the pharmaceutical preparations of the present invention for intranasal administration is desired to be as small as possible, in view of the irritant effects given on the administration site, yet certain abundance is desired as well, since there will be loss of the pharmaceutical preparations nebulized onto other places than the nasal mucosa. Considering the workability of the encapsulation, it is desired to be 15 mg or more. Accordingly, the weight per 1 capsule is 15–50 mg, preferably 15–30 mg, more preferably 15–25 mg. The mixing ratio of the adsorbent resin carrier and the biologically active peptide having pharmacological effects is not particularly limited, and it depends on what kinds of the adsorbent resin carrier powder and the biologically active peptide having pharmacological effects are used.

The biologically active peptide having pharmacological effects blended in the pharmaceutical preparations of the present invention are not particularly limited as far as they can be administered intranasally and they have weak topical irritation property, and their examples include a peptide hormone such as insulin, glucagon, calcitonin, gastrin, parathyroid hormone, angiotensin, growth hormone, secretin, lactotropic hormone (prolactin), thyrotropic hormone, melanocyte stimulating hormone, thyroid stimulating hormone (thyrotropin), luteinizing hormone stimulating hormone, human menopausal gonadotrophin (HMG), vasopressin, oxitocin, protirelin, corticotropin, and somatropin, a biologically active protein such as growth hormone stimulating factor (somatostatin), G-CSF, erythropoietin, EGF, interferon, and interleukin, and an enzyme such as SOD and a derivative thereof, urokinase, and lysozyme, and each drug may have the following effective dose.

| Biologically active peptides | Effective dose having pharmacological effects adhered on carrier powder of 15–50 mg |
|---|---|
| insulin | 10–80 units |
| calcitonin | 10–100 units |
| elcatonin | 10–100 units |
| salmon calcitonin | 10–100 units |
| Buserelin acetate (Gn-RH derivative) | 0.1–1 mg |
| Leuprorelin acetate (LH-RH derivative) | 0.1–1 mg |
| somatropin | 4–60 IU |
| glucagon | 1–10 mg |

A drug to be mixed with the adsorbent resin powder according to the present invention is not limited to the biologically active peptide having pharmacological effects, but it can be a drug having an electrostatic charge other than the biologically active peptide having pharmacological effects.

In order to maintain each pharmaceutical preparation of the present invention stably, a stabilizer can be added, and in some cases, when the absolute weight of the drug is too little to carry out accurate mixing procedure, an extender such as a protein including gelatin, gelatin succinate, decomposed gelatin and human serum albumin, an amino acid including aspartic acid and the like, and saccharides such as mannitol can be added, and the process for mixing these stabilizers or extenders with drugs is not particularly limited. The mixing ratio of the extender to each drug is not particularly limited either.

In order to raise the fluidity as the powder, a lubricant, illustratively talc, leucine, magnesium stearate and the like can be added to the pharmaceutical preparation of the present invention in an amount of 0.1–3% by weight.

These and other features, objects, and advantages of the present invention will become apparent upon reading the following description thereof, together with reference to the accompanying drawings.

DESCRIPTION OF THE PREFERRED EMBODIMENTS

Examples and Experimental Examples are given as follows, but those are not to be construed to limit the present invention.

EXAMPLE 1

100 g of dried insulin powder (about 25 units per 1 mg) and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 300 g of the carrier powder was further added and mixed in the similar way for 20 more minutes, then 400 g of the carrier powder and 20 g of magnesium stearate as a lubricant were added thereto and mixing was carried out in the similar manner for 20 more minutes to provide the pharmaceutical preparation of the present invention. 20 mg of the pharmaceutical preparation which is equivalent to 50 units insulin (2 mg insulin) was filled in a hard gelatin capsule of JP No. 4, packaged in PTP then put in an aluminum bag to prepare a final product. The product is administered to human intranasally using Puverizer.

EXAMPLE 2

100 g of insulin powder (about 25 units per 1 mg) and 50 g of gelatin were homogeneously mixed with 100 ml of water and dried by vacuum dehydration to provide a powder. The resulting powder and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 300 g of the carrier powder was further added and mixed in the similar way for 20 more minutes, then 350 g of the carrier powder and 20 g of magnesium stearate as a lubricant were added thereto and mixing was carried out in the similar manner for 20 more minutes to provide the pharmaceutical preparation of the present invention. 20 mg of the pharmaceutical preparation which is equivalent to 50 units insulin (2 mg insulin) was filled in a hard gelatin capsule of JP No. 4, packaged in PTP then put in an aluminum bag to produce a final product. The product is administered to human intranasally using Puverizer.

EXAMPLE 3

100 g of dried insulin powder (about 25 units per 1 mg) and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 20 g of human serum albumin and 200 g of the above-mentioned powder carrier were added thereto and mixed in the similar way for 20 minutes. 480 g of the above-mentioned carrier powder and 20 g of magnesium stearate as a lubricant were further added and mixing was carried out in the similar manner for 20 minutes to provide the pharmaceutical preparation of the present invention. 20 mg of the pharmaceutical preparation which is equivalent to 50 units insulin (2 mg insulin) was filled in a hard gelatin capsule of JP No. 4, packaged in PTP then put in an aluminum bag to produce a final product. The product is administered to human intranasally using Puverizer.

EXAMPLE 4

100 g of dried glucagon powder and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 300 g of the carrier powder was further added and mixed in the similar way for 20 more minutes, then 400 g of the carrier powder and 20 g of magnesium stearate as a lubricant were added thereto and mixing was carried out in the similar manner for 20 more minutes to provide the pharmaceutical preparation of the present invention. 20 mg of the pharmaceutical preparation which is equivalent to 2 mg glucagon was filled in a hard gelatin capsule of JP No. 4, packaged in PTP then put in an aluminum bag to produce a final product. The product is administered to human intranasally using Puverizer.

EXAMPLE 5

100 g of glucagon powder and 50 g of gelatin were homogeneously mixed with 100 ml of water and dried by vacuum dehydration to provide a powder. The resulting powder and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 300 g of the carrier powder was further added and mixed in the similar way for 20 more minutes, then 350 g of the carrier powder and 20 g of magnesium stearate as a lubricant were added thereto and mixing was carried out in the similar manner for 20 more minutes to provide the pharmaceutical preparation of the present invention. 20 mg of the pharmaceutical preparation which is equivalent to 2 mg glucagon was filled in a hard gelatin capsule of JP No. 4, packaged in PTP then put in an aluminum bag to produce a final product. The product is administered to human intranasally using Puverizer.

EXAMPLE 6

100 g of dried glucagon powder and 200 g of dried styrene-divinylbenzene copolymer resin having an average particle size of 30 μm as a powder carrier were placed in an agate ball mill mortar and subjected to rotational mixing at a room temperature under dry condition for 10 minutes and mixed homogeneously. 20 g of human serum albumin and 200 g of the above-mentioned powder carrier were further added and mixed in the similar way for 20 minutes. 480 g of the above-mentioned powder carrier and 20 g of magnesium stearate as a lubricant were added thereto and mixing was carried out in the similar manner for 20 more minutes to provide the pharmaceutical preparation of the present invention. 20 mg of the pharmaceutical preparation which is equivalent to 2 mg glucagon was filled in a hard gelatin capsule of JP No. 4, packaged in PTP then put in an aluminum bag to produce a final product. The product is administered to human intranasally using Puverizer.

EXPERIMENTAL EXAMPLE 1: Intranasal Administration Test of Insulin Preparations of the Present Invention on Rabbits (Preparation of Samples)

A styrene-divinylbenzene copolymer resin or polymethacrylate resin powder was sieved to get a fraction of 20–45 μm, which was sufficiently dried in desiccator and used as a resin carrier. Under dry condition, 20 mg of insulin was placed in an agate mortar and 40 mg of the resin carrier was added thereto and mixed for 10 minutes. Then 40 mg of the resin carrier was further added and mixed in the agate mortar under dry condition for 20 minutes. Then 100 mg of the carrier resin was added thereto and mixed in the agate mortar under dry condition for 30 minutes, and 5 mg of magnesium stearate was added and mixed in the agate mortar for an appropriate length of time. 10 mg of the resin carrier/insulin mixed powder product obtained according to the above-mentioned process was filled in one capsule (about 25 U in terms of insulin) to prepare a sample.

(Method)

Four rabbits were sedated by subcutaneously administering diazepam at 3 mg/kg and 1 capsule of each pharmaceutical preparation was nebulized into the nasal cavity using Puverizer (a product available from Teijin Ltd.) which had been remade for intranasal administration for rabbits. The blood glucose level was measured before administration, 15, 30, 45, 60, 90, 120, 150, 180, 240, 300 and 360 minutes after administration using a blood sugar measuring instrument (Glucoster M, a product available from Miles Sankyo K.K.). At the same time, blood sample was collected from a rabbit's ear vein into a micro test tube containing 50 μl of 3% EDTA, and it was centrifuged at 15000 rpm for 10 minutes to prepare a sample for insulin measurement.

(Results)

Figure 1A:
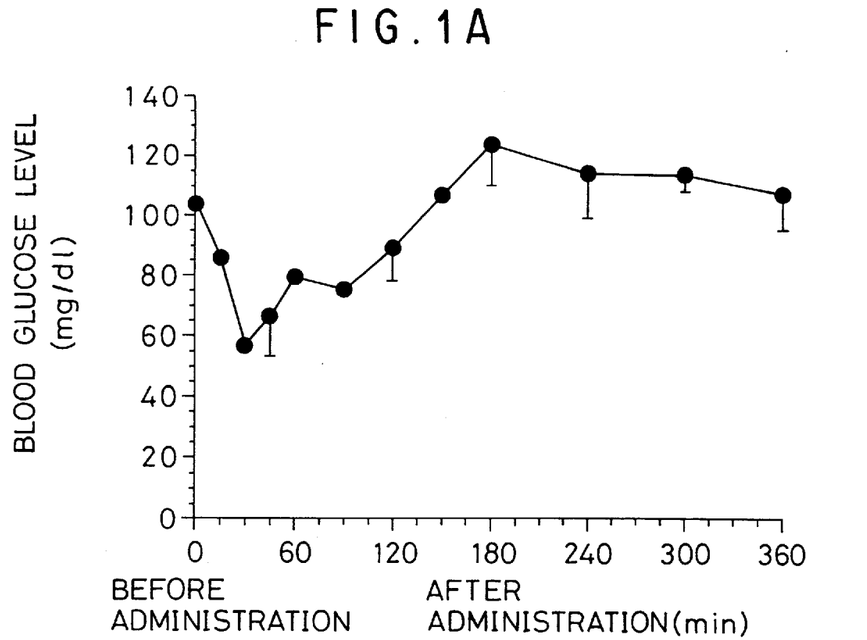
FIG. 1A is a graph showing the change of the blood glucose level with time after administration of styrene-divinylbenzene copolymer resin/insulin mixed product.
Figure 1B:
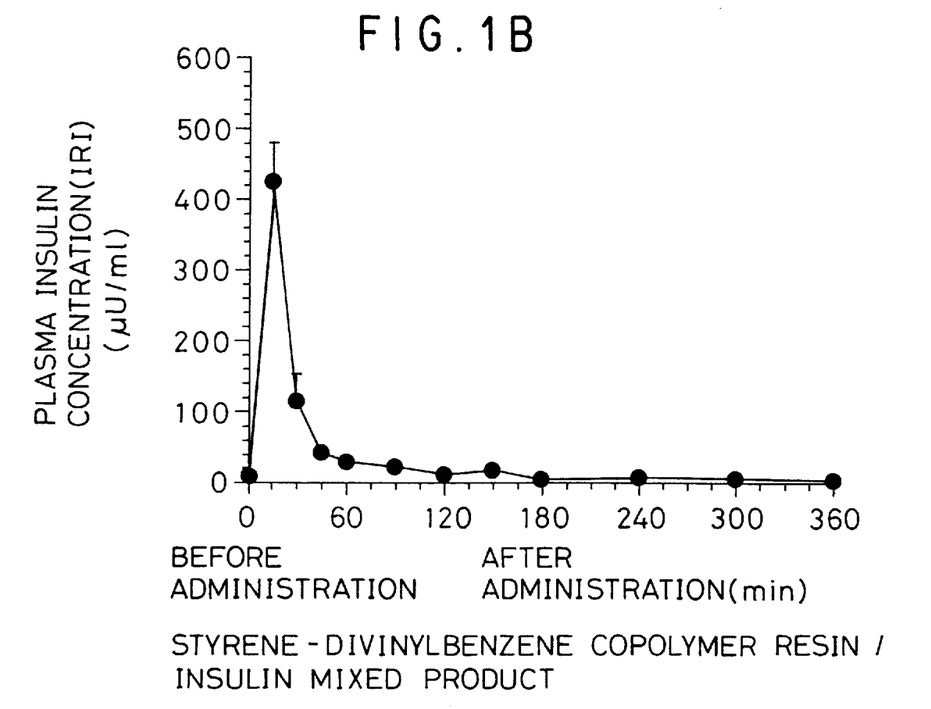
FIG. 1B is a graph showing the change of the plasma insulin concentration with time after administration of styrene-divinylbenzene copolymer resin/insulin mixed product.
Figure 2A:
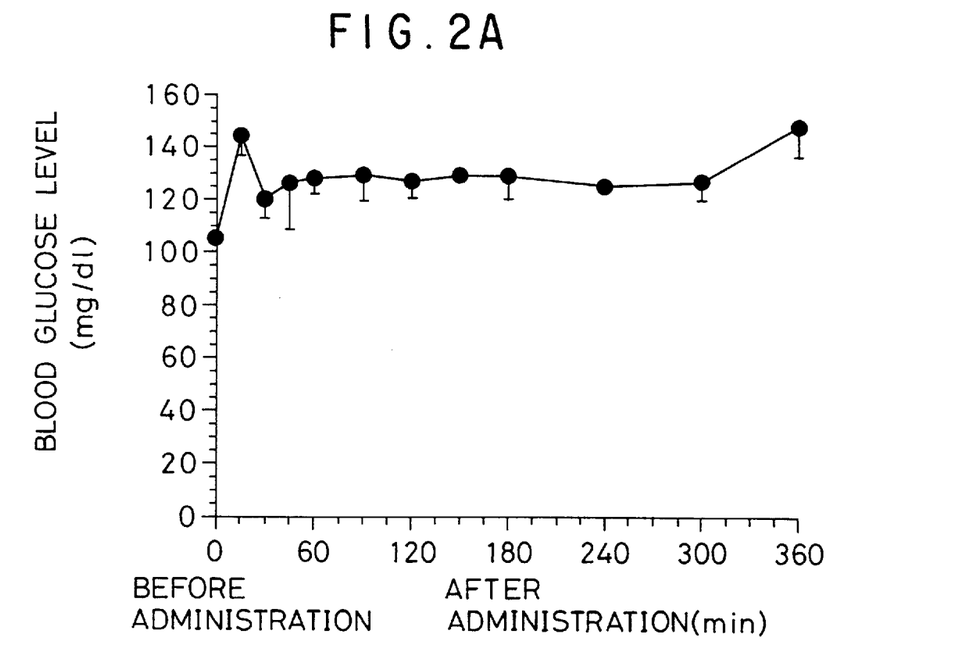
FIG. 2A is a graph showing the change of the blood glucose level with time after administration of polymethacrylate resin/insulin mixed product.
Figure 2B:
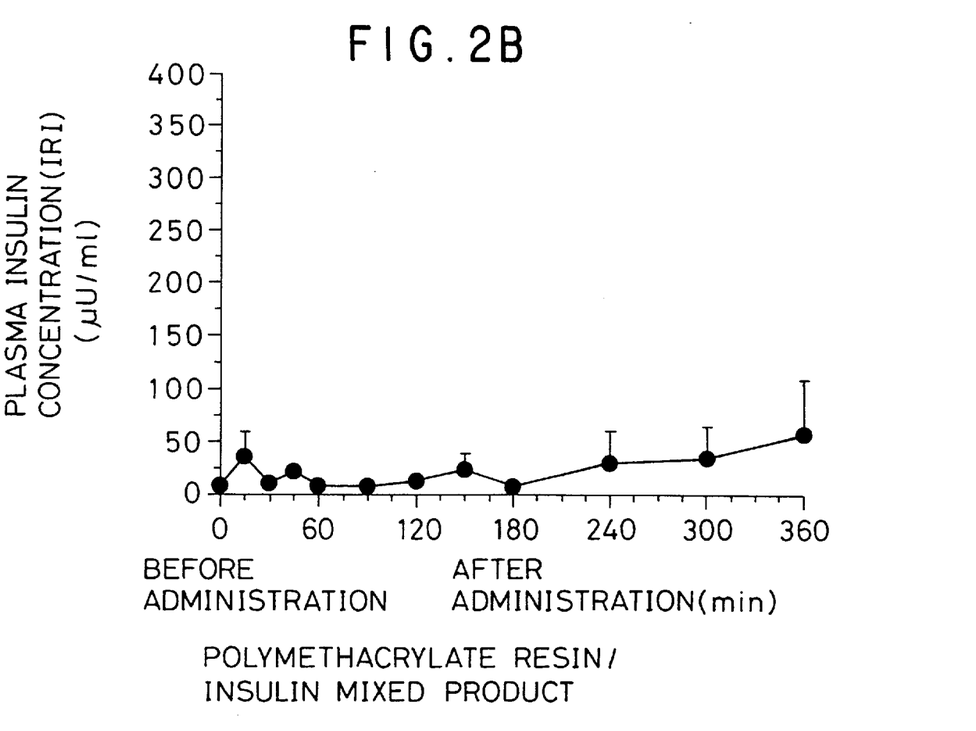
FIG. 2B is a graph showing the change of the plasma insulin concentration with time after administration of polymethacrylate resin/insulin mixed product.

The change of the blood glucose level with time after administration of styrene-divinylbenzene copolymer resin/ insulin mixed product is shown in FIG. 1A and the change of the plasma insulin concentration with time is shown in FIG. 1B, the change of the blood glucose level with time after administration of polymethacrylate resin/insulin mixed product is shown in FIG. 2A and the change of the plasma insulin concentration with time is shown in FIG. 2B. The average blood glucose level prior to the administration (103.5±3.5 mg/dl) reached the minimum (56.5±0.5 mg/dl) in 30 minutes, i.e. it was lowered by 45.5% compared to the level prior to the administration. The hypoglycemic action lasted for 120 minutes. On the other hand, the plasma insulin concentration showed the maximum of 425±55$\mu$ U/ml, 15 minutes after the administration, then gradually decreased. As for the polymethacrylate resin/insulin mixed product, no reduction in the blood glucose level was observed 15 minutes and 30 minutes after the administration. The plasma insulin concentration showed only a slight increase of 35±24$\mu$ U/ml 15 minutes after the administration.

EXPERIMENTAL EXAMPLE 2

A Intranasal Administration Test of Insulin Preparations of the Present Invention on Normal Adults (1)

(Preparation of Samples)

A styrene-divinylbenzene copolymer resin or polymethacrylate resin powder was sieved to get a fraction of 20–45 $\mu$m, which was sufficiently dried in desiccator and used as a resin carrier. Under dry condition, 40 mg of insulin was placed in an agate mortar and 40 mg of the resin carrier was added thereto and mixed for 10 minutes. Then 40 mg of the resin carrier was further added and mixed in the agate mortar under dry condition for 20 minutes. Then 100 mg of the carrier resin was added thereto and mixed in the agate mortar under dry condition for 30 minutes, and 5 mg of magnesium stearate was added and mixed in the agate mortar for an appropriate length of time. 10 mg of the resin carrier/insulin mixed powder product obtained according to the above-mentioned process was filled in one capsule (about 50 U in terms of insulin) to prepare a sample.

(Method)

Two normal male adults were the subjects, and they had been fasting overnight and one capsule of each pharmaceutical preparation was administered by nebulization into their nasal cavity using Puverizer (a product available from Teijin Ltd.) while they were hungry in early morning. The blood glucose level was measured before administration, and 10, 20, 30, 60 and 90 minutes after administration using a blood sugar measuring instrument (Glucoster M, a product available from Miles Sankyo K.K.). At the same time, blood sample was collected to prepare a sample for measurement of insulin in serum (IRI).

(Results)

Figure 3:
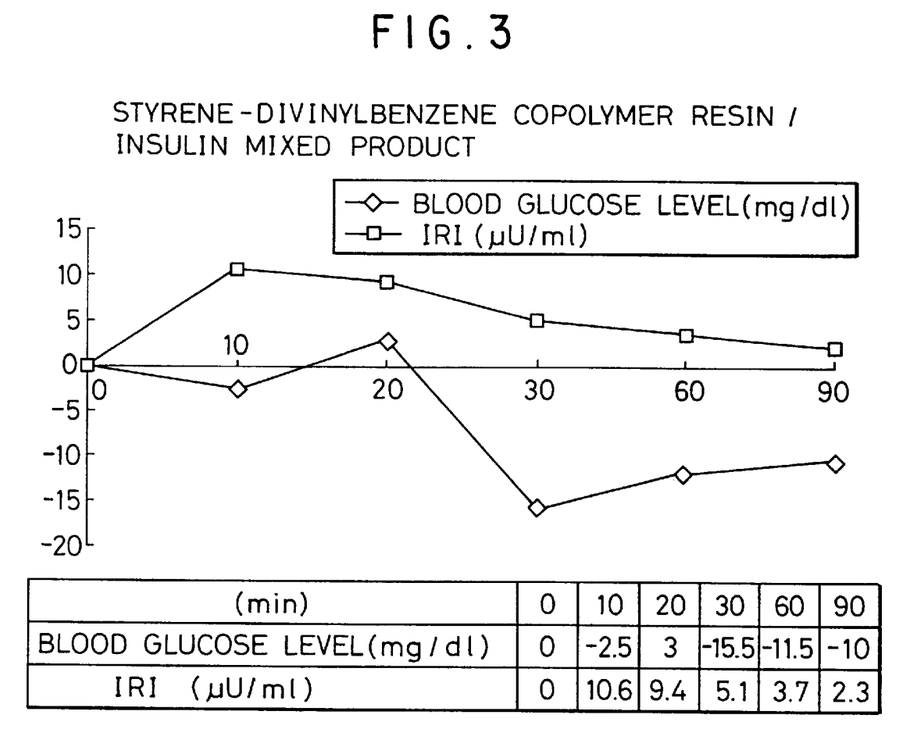
FIG. 3 is a graph showing the change of the blood glucose level and serum insulin concentration with time after administration of styrene-divinylbenzene copolymer resin/insulin mixed product.
Figure 4:
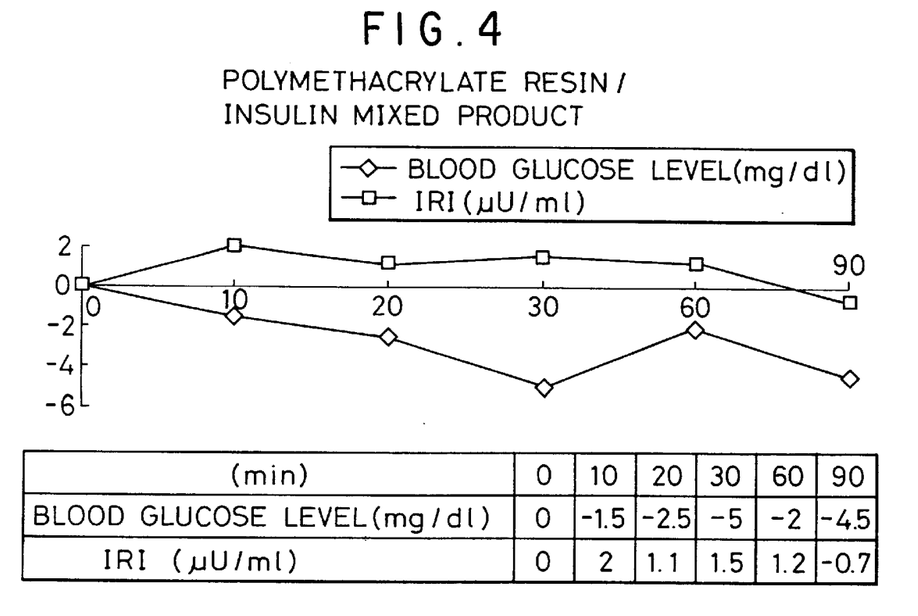
FIG. 4 is a graph showing the change of the blood glucose level and serum insulin concentration with time after administration of polymethacrylate resin/insulin mixed product.

An increase or decrease in the blood glucose level and that in the serum insulin concentration (IRI) after administration of styrene-divinylbenzene copolymer resin/insulin mixed product were calculated from the values prior to the administration and their changes with time are shown in FIG. 3 and those after the administration of the polymethacrylate resin/ insulin mixed product are shown in FIG. 4. The blood glucose level reached the minimum 30 minutes after the administration of styrene-divinylbenzene copolymer resin/ insulin mixed product, i.e. it was lower than the level prior to the administration by an average of 15.5 mg/dl. On the other hand, the serum insulin concentration (IRI) showed the maximum 10 minutes after the administration, i.e., it was increased from the level prior to the administration by an average of 10.6$\mu$ U/ml, then gradually decreased. After the administration of polymethacrylate resin/insulin mixed product, the blood glucose level showed only a slight decrease and the serum insulin concentration (IRI) showed only a slight increase as well. The results coincided well with those obtained with rabbits.

EXPERIMENTAL EXAMPLE 3

Intranasal Administration Test of Insulin Preparations of the Present Invention on Normal Adults (2)

Figure 5:
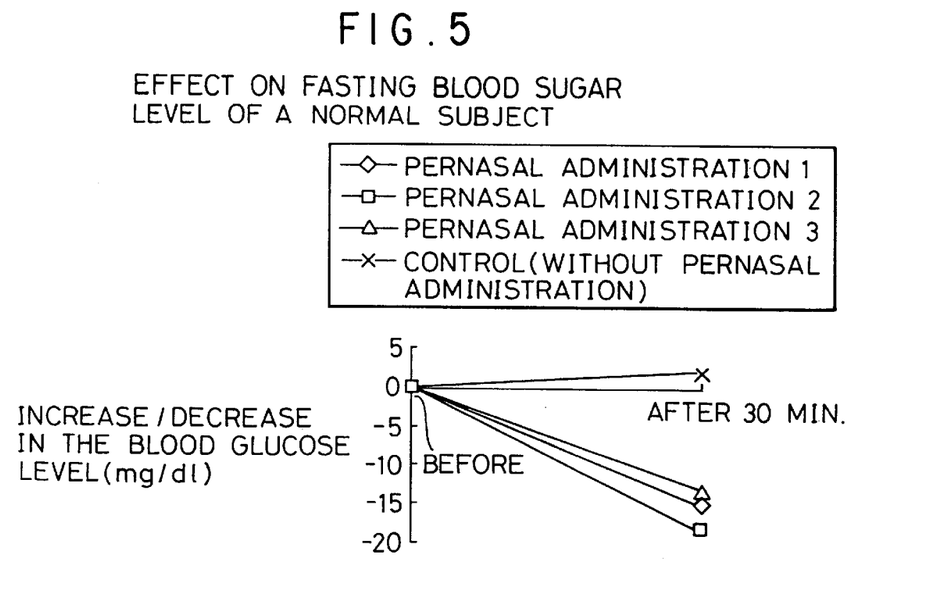
FIG. 5 is a graph showing the effect of the pharmaceutical preparation of the present invention on fasting blood sugar level in a normal subject.
Figure 7:
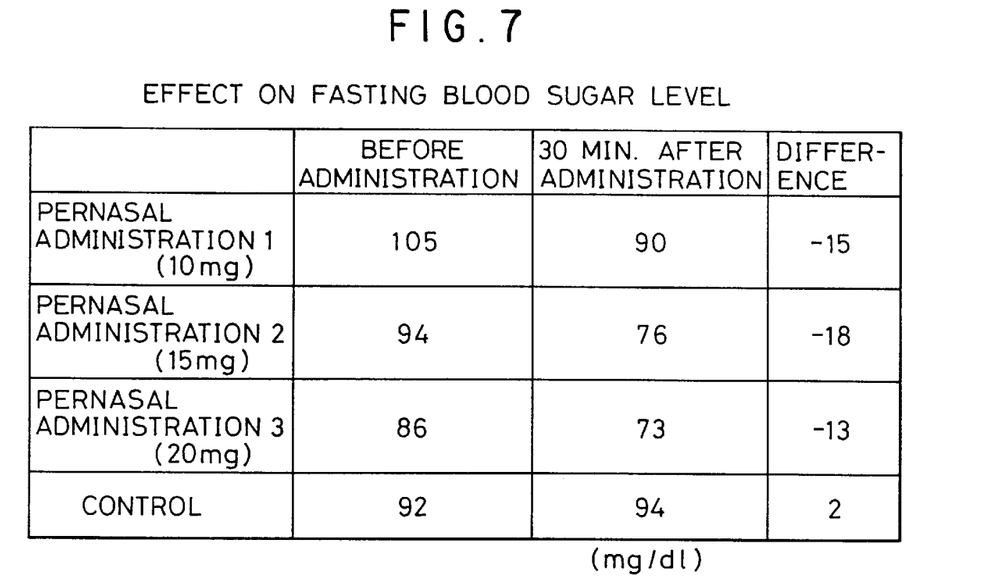
FIG. 7 is a table showing an effect of the pharmaceutical preparation of the present invention on fasting blood sugar level.

To confirm if the insulin concentration in the pharmaceutical preparation influences the hypoglycemic action or not, the same pharmaceutical preparation used in Experimental Example 2 (intranasal administration 1:10 mg of the pharmaceutical preparation containing 50 U of insulin), 15 mg of a pharmaceutical preparation containing 50 U of insulin (intranasal administration 2) and 20 mg of a pharmaceutical preparation containing 50 U of insulin (intranasal administration 3) were prepared and administered to the same normal subject under the same conditions used for the Experimental Example 2. The results of Experimental Example 2 have confirmed that the insulin preparations of the present invention show the max hypoglycemic action 30 minutes after the administration, the blood glucose level was measured 30 minutes after each administration; as a control, the blood glucose level was measured in the similar way at an interval of 30 minutes, without carrying out the intranasal administration. The results are shown in FIG. 5 and FIG. 7. The control showed no change in the blood glucose level, while with the intranasal administration 1, 2 and 3, the blood glucose level was decreased by 15, 18 and 13 mg/dl respectively and it was assumed that the insulin concentration in the pharmaceutical preparation does not affect the hypoglycemic action.

EXPERIMENTAL EXAMPLE 4

Intranasal Administration Test of Insulin Preparations of the Present Invention on Normal Adults (3)

Figure 6:
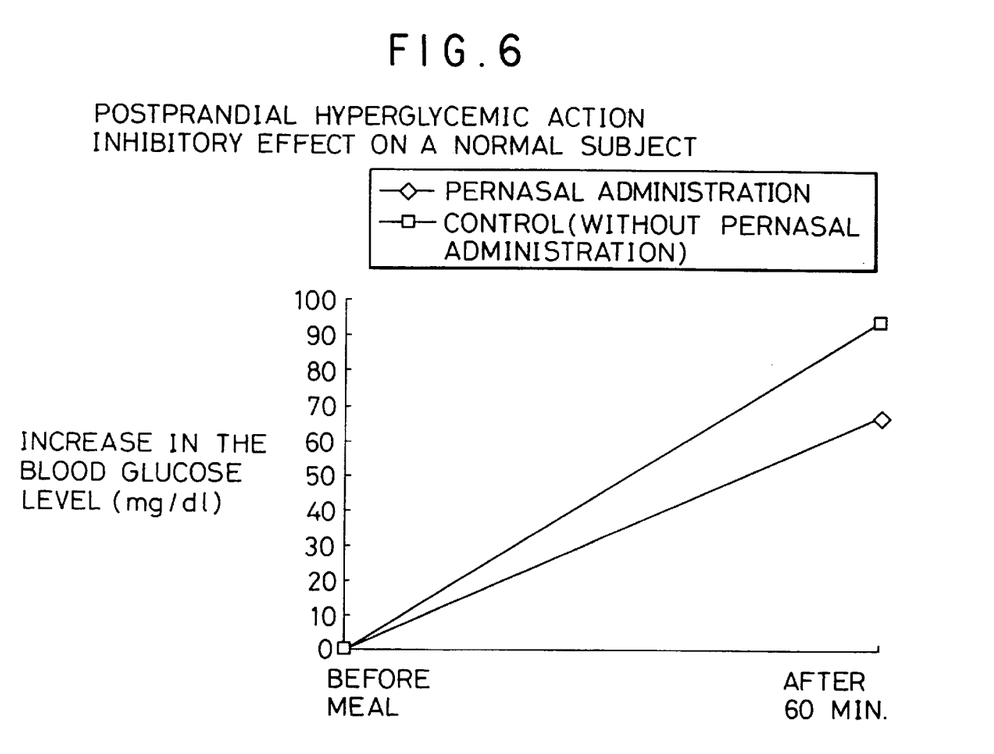
FIG. 6 is a graph showing postprandial hyperglycemic action inhibitory effect of the pharmaceutical preparation of the present invention on a normal subject.
Figure 8:
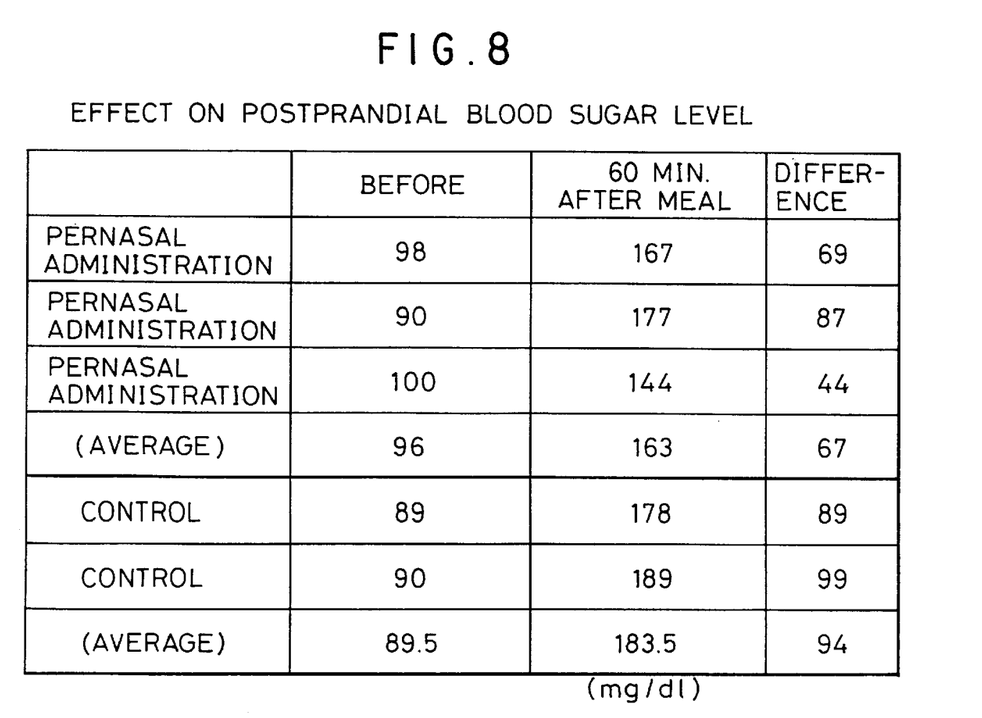
FIG. 8 is a table showing an effect of the pharmaceutical preparation of the present invention on postprandial blood sugar level.

We examined if the administration of the pharmaceutical preparations of the present invention can control the increase in the blood glucose level on normal subjects after dietary intake. The same normal subject was given one capsule of the pharmaceutical preparation of Experimental Example 2 by intranasal administration immediately after he/she had taken the same diet under the same conditions. The blood glucose level was measured 1 hour after the meal. Intranasal administration was carried out three times and as control the blood glucose level was measured twice without carrying out the intranasal administration. The results are shown in FIG. 6 and FIG. 8. The increase in the blood glucose level after no intranasal administration was 94 mg/dl on the average, but the blood glucose level after the intranasal administration was 67 mg/dl on the average and the increase of the blood glucose level was inhibited.

EXPERIMENTAL EXAMPLE 5

Ophthalmic Mucous Membrane Irritation Test

Figure 9:
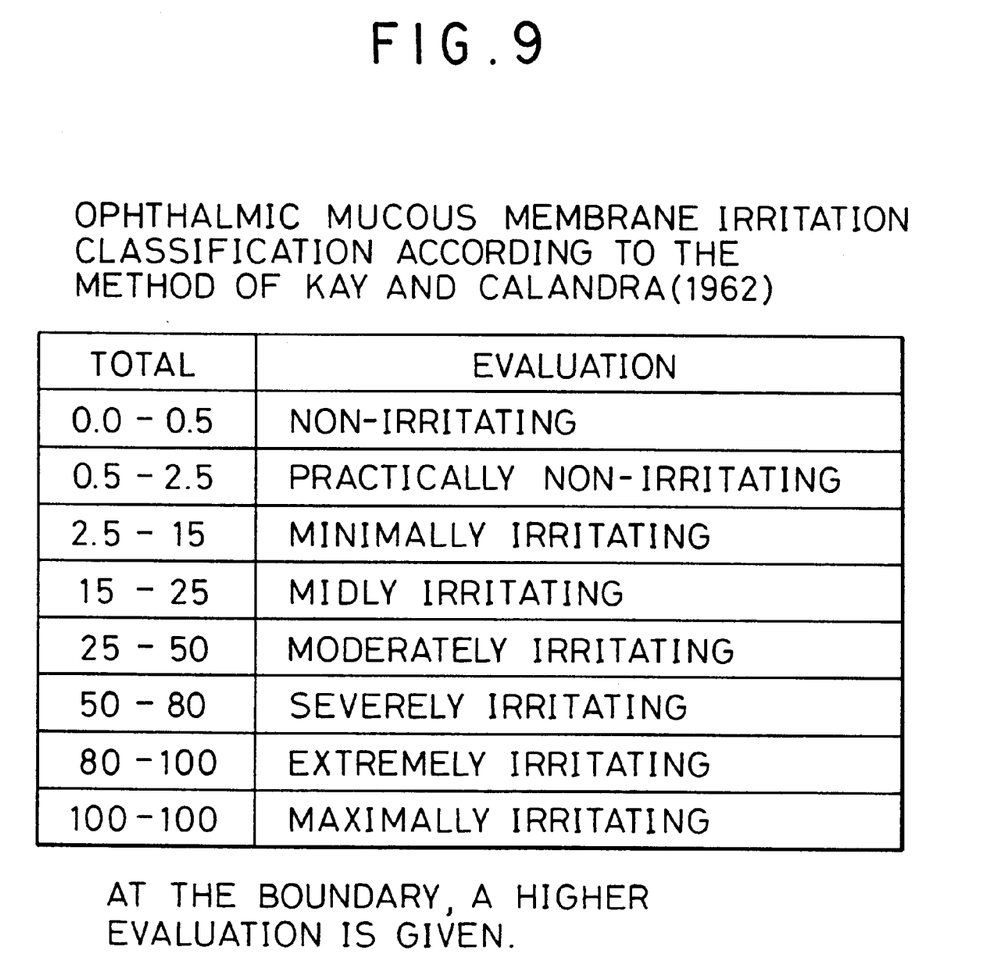
FIG. 9 is a table showing ophthalmic mucous membrane irritation classification according to the method of Kay and Calandra (1962).

As the carrier powder of the present invention is repeatedly administered to the nasal mucosa, it is an important element that the carrier powder does not have or have little irritant effects on the nasal mucosa. The irritant effects of the carrier powders used in Experimental Examples 1–4, i.e., styrene-divinylbenzene copolymer resin, sodium polystyrene sulphonate (cation exchange resin) and polymethacrylate resin, on a mucous membrane were examined by ophthalmic mucous membrane irritation test on rabbits. The testing method of the present test was based on the guidelines given by OECD. That means, 3 rabbits were used in this study, and a test drug was administered once into one eye of a rabbit in the conjunctival sac, and the other eye was used as control. The front part of the eye was observed with naked eyes and using slit lamp in all the cases 1, 24, 48 and 72 hours after the administration of the pharmaceutical preparation. Eyes were washed using lukewarm water of about 35° C. at the observation 24 hours after the administration. Scores of the conjunctival reaction obtained by administration of each test drug were calculated according to the assessment criteria of Draize method. The maximum of total score at each observation time was obtained for each test drug and for each test animal, and the average was calculated, then irritation evaluation in 8 stages (FIG. 9) was carried out according to the Kay and Calandra ophthalmic mucous membrane irritation classification method. As a result, the average value (score) of the maximum score of the styrene-divinylbenzene copolymer resin was 2.7, which corresponds to "Minimally irritating", the third level from the least irritating level among 8 levels, and sodium polystyrene sulphonate and polymethacrylate resin respectively had the score of 29.0, "Moderately irritating" (the fifth) and 3.3, "Minimally irritating" (the third). Styrene-divinylbenzene copolymer had very little irritating property, it is highly possible that the styrene-divinylbenzene copolymer can be repeatedly administered clinically.

It will become apparent to those skilled in the art that various modifications to the preferred embodiment of the present invention can be made without departing from the spirit and scope thereof as defined by the appended claims.

What is claimed is:

1. A dry pharmaceutical preparation for intranasal administration comprising a powder of a nonpolar adsorbent resin in admixture with a pharmacologically active compound, wherein the nonpolar adsorbent resin is styrene-divinylbenzene copolymer.

2. A pharmaceutical preparation for intranasal administration according to claim 1, wherein the particle size of the pharmacologically active compound is 10 μm–0.001 μm.

3. A pharmaceutical preparation for intranasal administration according to claim 1, wherein prior to the mixing, a biologically active peptide powder which has been dried under drying conditions is mixed with a dried powder of said nonpolar adsorbent resin.

4. A pharmaceutical preparation for intranasal administration according to claim 3, wherein after the mixing an aqueous solution or suspension of the biologically active peptide powder is mixed with a powder of styrene-divinylbenzene copolymer resin, then made into a powder by evaporation to dryness.

5. A pharmaceutical preparation for intranasal administration according to claim 3, wherein the pharmacologically active compound is a non-peptide pharmaceutical and wherein the pharmacologically active compound has an electrostatic charge.

6. A pharmaceutical preparation for intranasal administration according to claim 1, wherein an extender is added.

7. A pharmaceutical preparation for intranasal administration according to claim 1, wherein a lubricant is added.

8. A pharmaceutical preparation for intranasal administration according to claim 3, wherein the average particle size of the nonpolar adsorbent resin powder is 100 μm–10 μm.

9. The pharmaceutical preparation according to claim 3, wherein the pharmacologically active peptide is selected from the group consisting of insulin, glucagon, calcitonin, gastrin, parathyroid hormone, angiotensin, growth hormone, secretin, lactotropic hormone, thyrotropic hormone, melanocyte stimulating hormone, thyroid stimulating hormone, luteinizing hormone stimulating hormone, human menopausal gondotropin, vasopressin, oxytocin, protirelin, corticotropin, and somatotropin.

10. A dry pharmaceutical preparation for intranasal administration comprising a powder of a nonpolar adsorbent resin in admixture with a pharmacologically active peptide or protein.

11. A pharmaceutical preparation according to claim 10 which is obtained by mixing a dry powder of a nonpolar adsorbent resin with a pharmacologically active peptide or protein that has been dried prior to mixing.

12. A pharmaceutical preparation for intranasal administration according to claim 10, wherein the particle size of the biologically active peptide or protein is from 0.001 μm to 10 μm.

13. A pharmaceutical preparation according to claim 10 which is obtained by mixing the nonpolar adsorbent resin with a pharmacologically active peptide or protein and subsequently drying the resulting resin.

14. A pharmaceutical preparation for intranasal administration according to claim 10, wherein the average particle size of the adsorbent resin powder is 100 μm–10 μm.

15. The pharmaceutical preparation according to claim 10, wherein the pharmacologically active peptide is selected from the group consisting of insulin, glucagon, calcitonin, gastrin, parathyroid hormone, angiotensin, growth hormone, secretin, lactotropic hormone, thyrotropic hormone, melanocyte stimulating hormone, thyroid stimulating hormone, luteinizing hormone stimulating hormone, human menopausal gonadotropin, vasopressin, oxytocin, protirelin, corticotropin, and somatotropin.

16. The pharmaceutical preparation according to claim 10, wherein the pharmacologically active protein is selected from the group consisting of growth hormone stimulating factor, G-CSF, erythropoietin, EGF, interferon and interleukin.

17. The pharmaceutical preparation according to claim 10, wherein the protein is an enzyme selected from the group consisting of SOD, urokinase and lysozyme.

18. The pharmaceutical preparation according to claim 10, wherein the powder of the nonpolar adsorbent resin and the pharmacologically active peptide have both been dried prior to mixing.

19. A dry pharmaceutical preparation according to claim 10, wherein said nonpolar adsorbent resin is styrene-divinylbenzene copolymer resin.

20. A dry pharmaceutical preparation according to claim 10, which is obtained by a process comprising mixing a dry powder of a pharmaceutically active peptide with a dry powder of the nonpolar adsorbent resin in the presence of an organic solvent.

21. A pharmaceutical preparation for intranasal administration according to claim 20, wherein the organic solvent is ethanol.

22. A pharmaceutical preparation for intranasal administration according to claim 20, wherein an extender is added.

23. A pharmaceutical preparation for intranasal administration according to claim 22, wherein a lubricant is added.

* * * * *

UNITED STATES PATENT AND TRADEMARK OFFICE
CERTIFICATE OF CORRECTION

PATENT NO. : 5,948,749
DATED : September 7, 1999
INVENTOR(S) : Igarashi et al.

It is certified that error appears in the above-identified patent and that said Letters Patent is hereby corrected as shown below:

Column 1, lines 51 and 54:

"an other" should be - -another - -;

Column 10, claim 9, line 8:

"gondotropin" should be - -gonadotropin- -.

Signed and Sealed this

Twentieth Day of June, 2000

Q. TODD DICKINSON

*Attest:*

*Attesting Officer*    *Director of Patents and Trademarks*